United States Patent
Govari (10) Patent No.: US 7,854,733 B2
(45) Date of Patent: *Dec. 21, 2010

(54) PHASED-ARRAY FOR TISSUE TREATMENT

(75) Inventor: Assaf Govari, Haifa (IL)

(73) Assignee: Biosense Webster, Inc., Diamond Bar, CA (US)

( * ) Notice: Subject to any disclaimer, the term of this patent is extended or adjusted under 35 U.S.C. 154(b) by 806 days.

This patent is subject to a terminal disclaimer.

(21) Appl. No.: 10/807,979

(22) Filed: Mar. 24, 2004

(65) Prior Publication Data

US 2005/0215990 A1     Sep. 29, 2005

(51) Int. Cl.
A61B 18/18    (2006.01)
A61B 8/12     (2006.01)
(52) U.S. Cl. ............... 606/27; 600/459; 601/3
(58) Field of Classification Search ........... 606/27–52, 606/1; 600/439, 459; 601/2, 3
See application file for complete search history.

(56) References Cited

U.S. PATENT DOCUMENTS

| | | | |
|---|---|---|---|
| 5,273,045 A * | 12/1993 | Chihara et al. .......... 600/463 |
| 5,295,484 A * | 3/1994 | Marcus et al. ........... 600/439 |
| 5,331,947 A * | 7/1994 | Shturman ................ 600/115 |
| 5,391,140 A | 2/1995 | Schaetzle et al. |
| 5,590,657 A * | 1/1997 | Cain et al. ............... 600/439 |
| 5,630,837 A * | 5/1997 | Crowley .................. 601/2 |
| 5,938,660 A | 8/1999 | Swartz et al. |
| 6,004,269 A * | 12/1999 | Crowley et al. ......... 600/439 |
| 6,059,731 A * | 5/2000 | Seward et al. ........... 600/459 |
| 6,066,096 A * | 5/2000 | Smith et al. ............. 600/439 |
| 6,117,101 A * | 9/2000 | Diederich et al. ....... 604/22 |
| 6,245,020 B1 * | 6/2001 | Moore et al. ............ 600/466 |
| 6,251,109 B1 | 6/2001 | Hassett et al. |
| 6,416,511 B1 | 7/2002 | Lesh et al. |
| 6,457,365 B1 | 10/2002 | Stephens et al. |
| 6,524,271 B2 | 2/2003 | Brisken et al. |
| 6,645,202 B1 * | 11/2003 | Pless et al. .............. 606/41 |
| 6,652,515 B1 * | 11/2003 | Maguire et al. ......... 606/41 |
| 6,669,655 B1 | 12/2003 | Acker et al. |
| 6,780,157 B2 * | 8/2004 | Stephens et al. ........ 600/466 |

(Continued)

FOREIGN PATENT DOCUMENTS

EP    1424100 A1    6/2004

(Continued)

OTHER PUBLICATIONS

Diederich C. J. et al: "The Feasibility of Using Electrically Focused Ultrasound Arrays to Induce Deep Hyperthermia Via Body Cavities"; IEEE Transactions on Ultrasonics, Ferroelectrics and Frequency control; May 1, 1991; pp. 207-219; vol. 38, No. 3; IEEE Inc. New York, US.

(Continued)

*Primary Examiner*—Michael Peffley
(74) *Attorney, Agent, or Firm*—Louis J. Capezzuto (57) ABSTRACT

Apparatus is provided for ablating tissue of a patient by applying ultrasound energy to the tissue. The apparatus is typically delivered to the targeted tissue via a catheter and includes an ultrasound array, which is adapted to be driven as a phased array to concentrate the ultrasound energy on the targeted tissue while avoiding surrounding tissue.

6 Claims, 4 Drawing Sheets

U.S. PATENT DOCUMENTS

| | | | |
|---|---|---|---|
| 6,971,394 B2 * | 12/2005 | Sliwa et al. | 128/898 |
| 2002/0111386 A1 | 8/2002 | Sekins et al. | |
| 2004/0102769 A1 * | 5/2004 | Schwartz et al. | 606/27 |
| 2004/0254570 A1 * | 12/2004 | Hadjicostis et al. | 606/27 |

FOREIGN PATENT DOCUMENTS

| | | |
|---|---|---|
| WO | WO 99/44519 A2 | 9/1999 |
| WO | WO 02/096501 A2 | 12/2002 |

OTHER PUBLICATIONS

Pappone C, Rosario S, Oreto G, Tocchi M, Gugliotta F, Vicedomini G, Salvati A, Dicandia C, Mazzone P, Santinelli V, Gulletta S, Chierchia S. Circumferential Radiofrequency Ablation of Pulmonary Vein Ostia: A New Anatomic Approach for Curing Atrial Fibrillation. Circulation 2000; 102:2619-2628.

Natale A; Pisano E, Shewchik J, Bash D, Fanelli R, MD; Potenza D; Santarelli P; Schweikert R; White R; Saliba W; Kanagaratnam L; Tchou P; Lesh M. First Human Experience With Pulmonary Vein Isolation Using a Through-the-Balloon Circumferential Ultrasound Ablation System for Recurrent Atrial Fibrillation Circulation 2000; 102;1879-1882.

Foreign Communication 05 251 801.6-1265 Ref. P040032EP dated Feb. 26, 2008.

* cited by examiner

PHASED-ARRAY FOR TISSUE TREATMENT

FIELD OF THE INVENTION

The present invention relates generally to medical procedures and therapeutic devices. More specifically, the invention relates to the use of phased arrays for focusing energy on tissue to be treated in the course of therapeutic procedures.

BACKGROUND OF THE INVENTION

Atrial fibrillation is a significant and prevalent medical problem. Several nonpharmalogical percutaneous transcatheter therapeutic approaches have been specifically designed in attempts to solve this problem. One such approach is electrical isolation of the pulmonary veins, which is especially suitable for cases where autonomous foci in the pulmonary veins exist. These foci may trigger paroxysmal atrial fibrillation or may sustain the fibrillation.

The following references, which are incorporated herein by reference, may be useful:

Scheinman M M, Morady F. Nonpharmacological Approaches to Atrial Fibrillation. Circulation 2001;103: 2120-2125.

Pappone C, Rosanio S, Oreto G, Tocchi M, Gugliotta F, Vicedomini G, Salvati A, Dicandia C, Mazzone P, Santinelli V, Gulletta S, Chierchia S. Circumferential Radiofrequency Ablation of Pulmonary Vein Ostia: A New Anatomic Approach for Curing Atrial Fibrillation. Circulation 2000; 102:2619-2628.

Natale A; Pisano E, Shewchik J, Bash D, Fanelli R, M D; Potenza D; Santarelli P; Schweikert R; White R; Saliba W; Kanagaratnam L; Tchou P; Lesh M. First Human Experience With Pulmonary Vein Isolation Using a Through-the-Balloon Circumferential Ultrasound Ablation System for Recurrent Atrial Fibrillation Circulation 2000;102:1879-1882.

U.S. Pat. No. 6,457,365 to Stephens, et al., whose disclosure is incorporated herein by reference, describes an ultrasound transducer array including at least one transducer element having first and second portions separated by an acoustical discontinuity. The first portion has the desired length to form a half-wave k31 resonance, while the second portion has a resonant length for an undesired very low frequency out-of-band k31 resonance. The thickness of the transducer element is designed for k33 half-resonance. Given the design, the transducer element can operate and provide for both forward-looking and side looking elevation apertures. A method is also disclosed for using the disclosed ultrasound transducer in ultrasound imaging.

U.S. Pat. No. 6,524,271 to Brisken, et al., whose disclosure is incorporated herein by reference, describes a method for treating a target region in a body lumen, including: directing a uniform dose of ultrasonic energy from an interior of the lumen radially outward over a treatment length of the lumen, wherein the dosage of ultrasonic energy received at any one point along the length varies by no more than plus or minus 6 decibels from that received at any other point along the length.

U.S. Pat. No. 6,416,511 to Lesh, et al., whose disclosure is incorporated herein by reference, describes a circumferential ablation device assembly, which is adapted to form a circumferential conduction block in a pulmonary vein.

U.S. Pat. No. 6,251,109 to Hassett, et al., whose disclosure is incorporated herein by reference, describes a process for treatment of atrial arrhythmia by ablation of pulmonary veins via an ablation catheter located within one of a pair of balloons secured to the catheter.

U.S. Pat. No. 6,117,101 to Diederich and Lesh, et al., whose disclosure is incorporated herein by reference, describes a circumferential ablation device which is adapted to form a circumferential conduction block in a pulmonary vein by producing a radial ultrasound signal inside a balloon such that the ultrasound signal couples to the balloon's outer skin and ablates tissue in contact with the balloon's outer skin.

U.S. Pat. No. 6,652,515 to Maguire et al., whose disclosure is incorporated herein by reference, describes a circumferential ablation device, which is adapted to form a circumferential conduction block in a pulmonary vein by applying thermal, light or ultrasound energy to ablate tissue. Directional control of ultrasound ablation is attempted through rotation of a planar ultrasound source or by applying various coatings to a balloon in which the ultrasound source is affixed.

U.S. Pat. No. 5,938,660 to Swartz, et al., whose disclosure is incorporated herein by reference, describes a process and devices for treating atrial arrhythmia by circumferential ablation of vessels including the pulmonary veins.

U.S. Pat. No. 5,295,484 to Marcus, et al., whose disclosure is incorporated herein by reference, describes a device for delivering ultrasonic energy to myocardial tissue so as to destroy myocardial tissue implicated in an arrhythmia.

SUMMARY OF THE INVENTION

An aspect of the present invention provides improved apparatus and methods for treating atrial fibrillation.

An aspect of the present invention provides improved methods and apparatus for transcatheter therapeutic approaches for electrical isolation of the pulmonary vein.

An aspect of the present invention provides methods and apparatus for selective ablation of tissue adjacent to the distal end of a catheter.

An aspect of the present invention provides methods and apparatus for accessing and imaging tissue via catheter and subsequently ablating a selected region of tissue.

An aspect of the present invention provides methods and apparatus for accessing and imaging solid tumors via catheter and subsequently ablating the tumor.

An aspect of the present invention provides methods and apparatus for accessing and imaging liver tumors via catheter and subsequently ablating the tumor.

An aspect of the present invention provides methods and apparatus for accessing and imaging fibroid tumors of the uterus via catheter and subsequently ablating the tumor.

In some embodiments of the present invention, a therapeutic catheter comprising an ultrasound device is introduced into a region of the body of a patient where imaging and/or tissue ablation is desired. Typically, the ultrasound device comprises an ultrasound transducer array, which comprises a plurality of ultrasound transducer elements and is circumferentially disposed around an axis of the catheter. Each ultrasound transducer element is coupled to a control unit via a control wire, such that the control unit coordinates the functioning of each transducer element in the array so that the array can function as a phased array. Such a phased array, in accordance with some embodiments of the present invention, provides the ability to concentrate energy in selected regions while reducing the energy applied to other regions. Thus, a selected region of tissue is treated, while other tissue in close proximity to the selected region is less affected or even substantially unaffected by the treatment of the selected region of tissue. For example, the phased array may be actuated to generally ablate tissue from 0 degrees to 330 degrees with respect to the catheter axis, and to generally avoid ablating tissue from 331 degrees to 359 degrees.

For some applications, the catheter comprises an anchoring balloon near the distal end of the catheter, such that inflating the balloon with a fluid anchors the distal end of the catheter in a desired location. The ultrasound device is typically, but not necessarily, located inside the anchoring balloon, such that the device can be fixed adjacent to a desired region of tissue.

In some embodiments of the present invention, the therapeutic catheter is used to treat and/or prevent atrial fibrillation by electrical isolation of the pulmonary vein. Typically, the catheter is introduced into the left atrium and then into the pulmonary vein. Once the catheter is properly placed in the pulmonary vein, the anchoring balloon is inflated with fluid to hold the distal end of the catheter in the desired position. Typically, the distal portion of the anchoring balloon is inside the pulmonary vein while the proximal portion is protruding into the left atrial lumen. The ultrasound transducer array is typically positioned inside the anchoring balloon.

In some embodiments, the ultrasound device comprises an ultrasound detector, which, combined with the ultrasound transducer array, functions as an imaging system such that the tissue surrounding the anchoring balloon is imaged before treatment commences. This allows for the identification of anatomical structures that either: (a) are targeted for treatment or (b) it is desirable to avoid damaging. For example, during electrical isolation of the pulmonary vein it is desirable to avoid damaging the phrenic nerve, which is integral to breathing and passes close to the region where the pulmonary vein joins the left atrium and where the ultrasound device may be placed. For some applications, the phrenic nerve is located prior to electrical isolation of the pulmonary vein, such that subsequently the ultrasound transducer array is driven as a phased array so as to avoid directing damaging levels of energy to the region of the phrenic nerve.

In an embodiment, driving the cylindrical ultrasound transducer array as a phased array allows for control of both the azimuthal distribution of energy (e.g., 10 to 350 degrees) and the radial distribution of energy (e.g., 8 to 15 mm from the catheter axis), so that along with the ability to target or avoid certain azimuthal directions, the radial distance to the peak energy concentration is also controlled. Typically, the ultrasound energy is concentrated directly at the body tissue to be treated. In some embodiments of the present invention, the array of ultrasound transducers is used as a tumor ablation device to treat a solid tumor. To commence treatment, the therapeutic catheter is typically advanced through the venous system to the site of the tumor. Alternatively, a percutaneous approach is used to access the site of the tumor. For example, the liver can be accessed via any one of the superior vena cava, the portal vein, or the hepatic artery, but in some cases it may be difficult to access a particular tumor via any of these pathways making the percutaneous approach suitable. A tumor of the kidney may also be approached either through the venous system or percutaneously. Another common type of tumor that is amenable to treatment with the therapeutic catheter is a fibroid tumor of the uterus. In this case a transvaginal approach would be suitable, but a percutaneous approach may also be used.

To commence treatment of a tumor, the therapeutic catheter is typically advanced to the site of the tumor using techniques common in the art, for example under fluoroscopic or CAT scan guidance. Once the therapeutic catheter is sufficiently close to the tumor, the ultrasound transducer array and the ultrasound detector are typically used to obtain an image of the tumor and the tissue surrounding the tumor. Using the ultrasound images and/or the fluoroscopic or CAT scan guidance, the catheter is advanced to touch the tumor, and, for some applications, subsequently enter the tumor slightly. At this point the anchoring balloon is typically inflated to secure the catheter in place and the ultrasound device is advanced to press against the tumor. For some applications, another ultrasound image is obtained at this time, so the desired direction for the ultrasound transducer array to direct ultrasound energy can be determined.

Since the ultrasound device is pressed against a face of the tumor, the ultrasound transducer array typically comprises a two-dimensional array of transducer elements, arranged such that each transducer element comes in contact with the face of tumor. With this arrangement, substantially all of the ultrasound energy is directed towards the tumor; Alternatively, the transducer array is arranged to form a cone or hemisphere, such that mechanical pressure can be applied to advance the transducer array into the tumor prior to treating the tumor with ultrasound. These ultrasound array configurations may be used in addition to or instead of the circumferential ultrasound array described hereinabove.

Typically, an ultrasound image of the tumor and surrounding tissue is obtained subsequent to treatment, allowing a decision to be made as to whether more treatment is required. If more treatment is to be performed, typically the ultrasound image is used to reposition the ultrasound transducer array, if appropriate, for enhanced energy transfer to the tumor.

There is therefore provided, in accordance with an embodiment of the present invention, apparatus for use with a subject, including:

a catheter having a longitudinal axis and having a distal portion; and an ultrasound array fixed to the distal portion, adapted to operate in a phased array mode to apply ablating energy to tissue of the subject located in a range of azimuths, with respect to the longitudinal axis, that is less than 360 degrees.

Typically, but not necessarily, the ultrasound array includes between about 32 and 64 ultrasound transducers. Alternatively or additionally, the ultrasound array is adapted to apply the ablating energy to tissue in a range of azimuths between about 180 and 359 degrees.

In a typical embodiment, when the catheter is disposed in a vicinity of an ostium of a pulmonary vein of the subject, the range of azimuths is sufficiently smaller than 360 degrees to avoid inducing a deficit in a phrenic nerve of the subject. Typically, but not necessarily, the apparatus includes detection functionality, adapted to determine tissue of the subject that is not to be targeted by the ablating energy, wherein the ultrasound array is adapted to configure the ablating energy responsive to the determination of the tissue that is not to be targeted.

In some embodiments, the ultrasound array is adapted to set the range of azimuths responsive to the determination of the tissue that is not to be targeted.

Typically, but not necessarily, the detection functionality includes an ultrasound transducer. Additionally or alternatively, the detection functionality includes at least a portion of the ultrasound array.

In some embodiments the detection functionality includes imaging functionality.

Typically, the detection functionality is adapted to be fixed to the distal portion of the catheter. Alternatively, the detection functionality is adapted to operate external to a body of the subject.

There is further provided, in accordance with an embodiment of the present invention, a method for ablating tissue of a subject, including:

inserting an ultrasound array having an axis into a body of the subject, adjacent to the tissue; and actuating the ultrasound array in a phased array mode to apply ablating ultrasound energy to the tissue in a range of azimuths, with respect to the axis, that is less than 360 degrees.

In an embodiment, actuating the ultrasound array includes applying the ablating ultrasound energy in a range of azimuths that is greater than 180 degrees. For some applications, actuating the ultrasound array includes applying the ablating ultrasound energy in a range of azimuths that is greater than 270 degrees.

In an embodiment, inserting the ultrasound array includes placing the ultrasound array in a vicinity of an ostium of a pulmonary vein of the subject, and configuring the range of azimuths to be sufficiently smaller than 360 degrees to avoid inducing a deficit in a phrenic nerve of the subject.

For some applications, actuating the ultrasound array includes:

determining tissue of the subject that is not to be targeted by the ablating energy; and applying the ablating energy responsive to the determination of the tissue that is not to be targeted.

In an embodiment, applying the ablating energy includes setting the range of azimuths responsive to the determination of the tissue that is not to be targeted.

In an embodiment, determining the tissue that is not to be targeted includes transmitting non-ablating ultrasound energy at the tissue that is not to be targeted. For example, transmitting the non-ablating ultrasound energy may include transmitting the non-ablating ultrasound energy from an ultrasound transducer in the ultrasound array.

In an embodiment, determining the tissue that is not to be targeted includes imaging the tissue that is not to be targeted.

For some applications, determining the tissue includes performing a measurement in a vicinity of the ultrasound array. Alternatively or additionally, determining the tissue includes performing a measurement from a site external to a body of the subject.

The present invention will be more fully understood from the following detailed description of embodiments thereof, taken together with the drawings, in which:

DETAILED DESCRIPTION OF EMBODIMENTS

Figure 1:
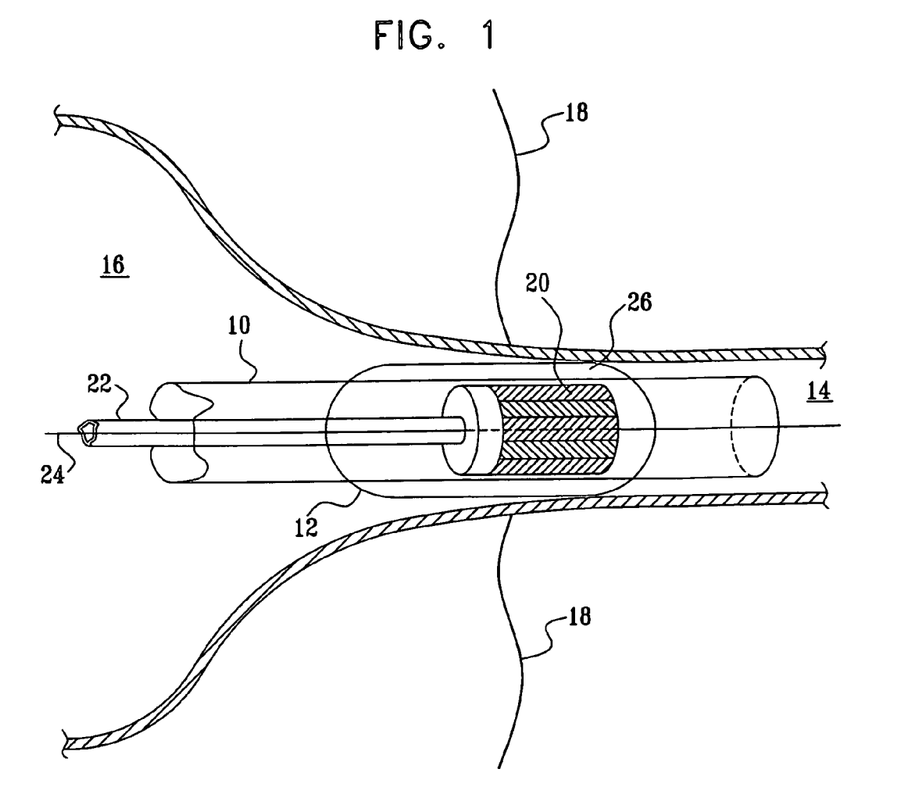
FIG. 1 is a schematic, partly sectional illustration showing the placement of a therapeutic catheter in the region where the pulmonary vein meets the left atrium, in accordance with an embodiment of the present invention.

FIG. 1 is a schematic, partly sectional illustration showing the placement of a therapeutic catheter 10 in the region where a pulmonary vein 14 meets the left atrium 16, in accordance with an embodiment of the present invention. Typically, catheter 10 is directed to the region where the pulmonary vein meets the left atrium by first threading a guide wire 24 through the venous system of the patient to the desired location and subsequently threading catheter 10 over the guide wire. Alternatively, the catheter and guide wire are an integral unit, which is threaded through the venous system. Once catheter 10 is in the desired position, it is typically held in place by an anchoring balloon 12, which is inflated with a fluid 26 until the balloon is securely wedged against the surrounding tissue.

Typically, once catheter 10 is secured in the desired location, an ultrasound device 20 is fed through catheter 10 by pushing on a lead 22, which is coupled to device 20. Lead 22 possesses the requisite stiffness and flexibility to allow a healthcare professional to push device 20 to a location inside anchoring balloon 12. In some embodiments, lead 22 and device 20 comprise a hollow core such that device 20 and lead 22 can be passed over guide wire 24. In some other embodiments of the present invention, ultrasound device 20 and lead 22 are coupled to catheter 10 such that ultrasound device 20 and catheter 10 are advanced into the heart simultaneously over guide wire 24. In still other embodiments of the present invention, guide wire 24 is fixed or otherwise coupled to catheter 10, such that guide wire 24 and catheter 10 are advanced simultaneously.

Figure 2:
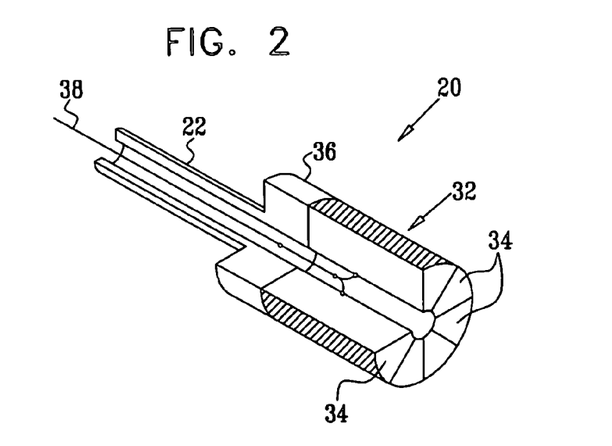
FIG. 2 is a schematic illustration of an ultrasound device, in accordance with an embodiment of the present invention.

FIG. 2 shows a schematic, illustration of ultrasound device 20, in accordance with an embodiment of the present invention. Typically, device 20 comprises an ultrasound array 32, which comprises a plurality of ultrasound transducers 34 arranged circumferentially around device lead 22. In some embodiments, array 32 comprises any number of ultrasound transducers 34, for instance, from about thirty-two (32) to about sixty-four (64) elements, and e.g., forty-eight (48) ultrasound transducers 34, which are cut from a single crystal in one embodiment according to the present invention. In other embodiments, array 32 comprises a larger or smaller number of transducers 34, the number varying with the details of a specific application. Each transducer 34 is coupled via a wire to a control bus 38, which drives each of transducers 34, such that array 32 may function as a phased array.

By driving array 32 as a phased array, the ultrasound energy projected in any azimuthal direction can be controlled. Thus, certain tissue can be targeted for treatment, while other tissue can be left untreated, allowing the healthcare professional to only treat desired regions of tissue while avoiding substantial energy application to surrounding tissue.

Typically, ultrasound device 20 comprises an ultrasound detector 36, such that tissue near ultrasound device 20 is imaged prior to the initiation of treatment. This allows the healthcare professional to assess the location and orientation of device 20 and/or to analyze the surrounding tissue, in order to locate particular targets for ablation. Additionally, the effects of treatment can be assessed by imaging the surrounding tissue both during and after treatment. This capability is particularly useful, for example, in applications involving treatment of tumors discussed hereinbelow. For some applications, ultrasound detection functionality is incorporated in array 32. In an embodiment, other imaging or detection functionalities are incorporated in ultrasound device 20 or in another element, so as to facilitate assessments of tissue to target with ultrasound energy and tissue to avoid targeting with ultrasound energy.

In an embodiment, electrical isolation of pulmonary vein 14 is accomplished while avoiding damage to phrenic nerve 18 by reducing the amount of ultrasound energy projected in the direction of the phrenic nerve, but providing sufficient ultrasound energy in the other directions to cause sufficient ablation of the pulmonary vein.

Figure 3A:
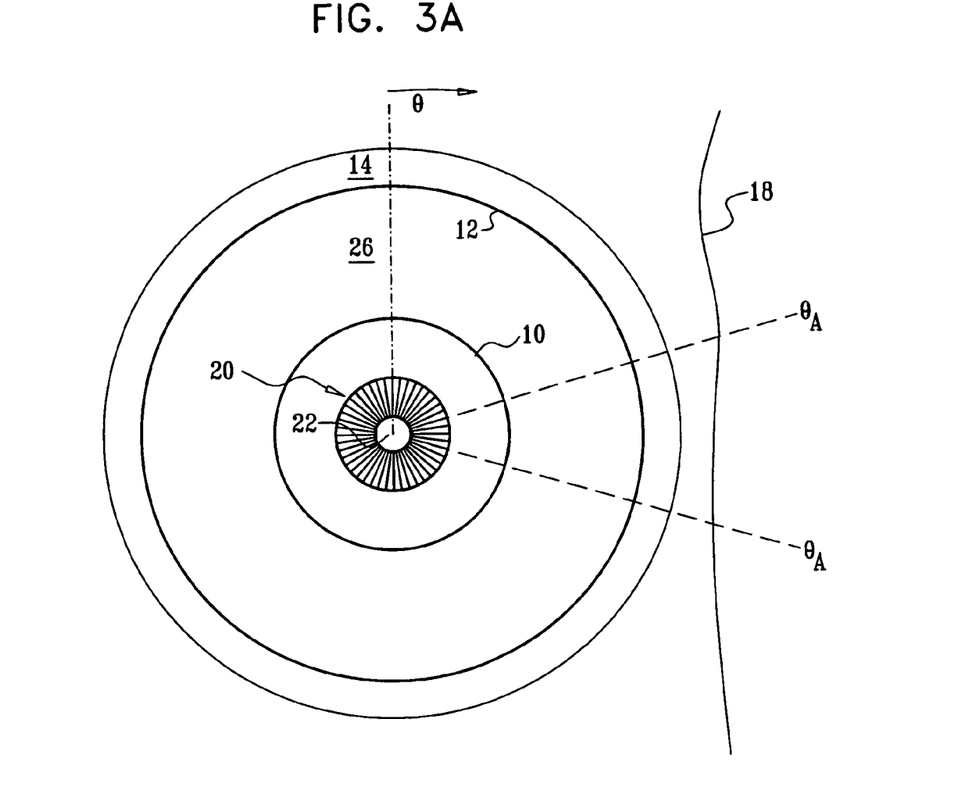
FIG. 3A is a schematic sectional illustration of a circumferential ultrasound phased array in a pulmonary vein, in accordance with an embodiment of the present invention.
Figure 3B:
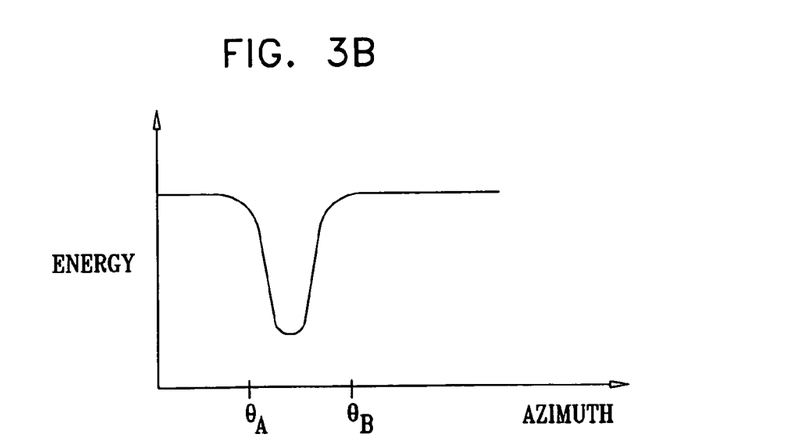
FIG. 3B is a sample graph showing a possible profile of the azimuthal energy distribution provided by the circumferential ultrasound phased array, in accordance with an embodiment of the present invention.

Reference is now made to FIGS. 3A and 3B. FIG. 3A is a schematic sectional illustration of ultrasound device 20 in pulmonary vein 14, in accordance with an embodiment of the present invention. FIG. 3B is a sample graph of ultrasound energy applied to the pulmonary vein due to the activation of array 32 as a phased array, in accordance with an embodiment of the present invention. As shown in FIG. 3B, relatively less energy is applied in the regions close to phrenic nerve 18. Typically, the ultrasound energy is focused on the vessel wall where ablation is desired.

Figure 4:
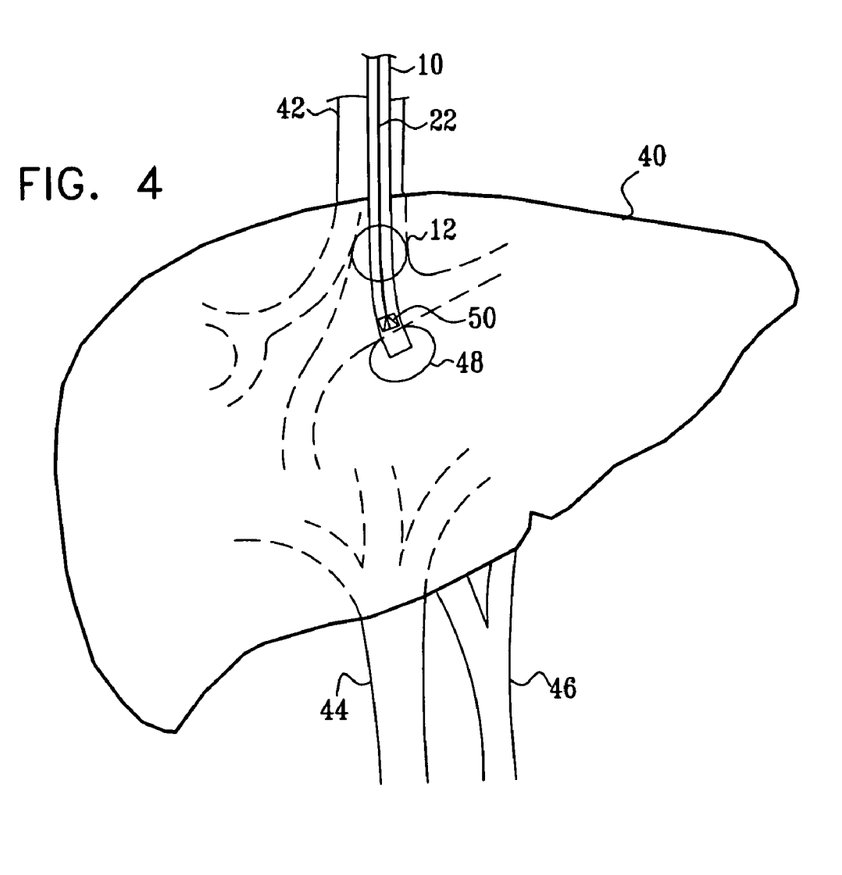
FIG. 4 is a schematic, sectional illustration showing the placement of the therapeutic catheter adjacent to a liver tumor, in accordance with an embodiment of the present invention.
Figure 5A:
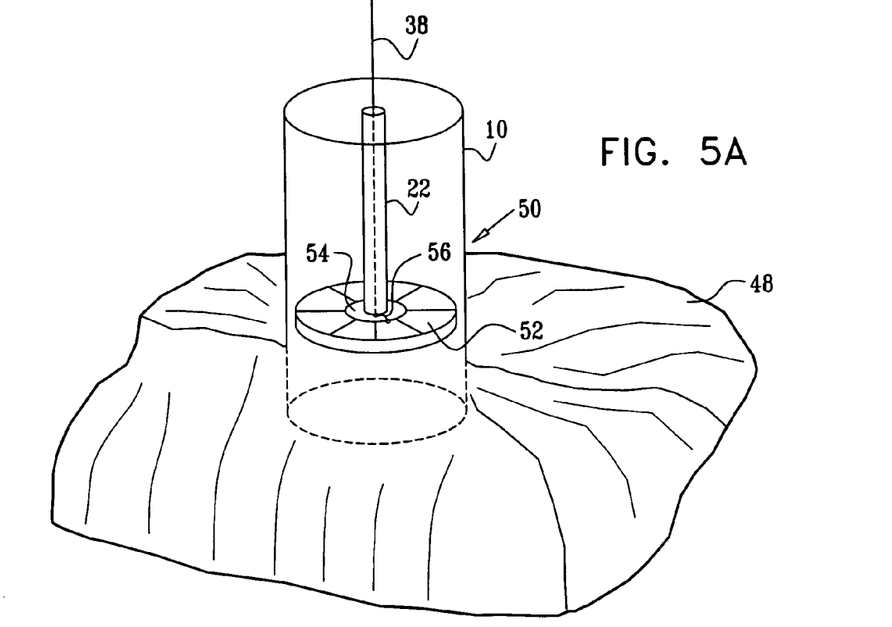
FIGS. 5A and 5B are schematic, illustrations of tumor ablation devices for treating a solid tumor in accordance with respective embodiments of the present invention.

FIG. 4 is a schematic, sectional illustration showing the placement of a tumor ablation device 50 adjacent to a liver tumor 48, via therapeutic catheter 10, in accordance with an embodiment of the present invention. Therapeutic catheter 10 is illustrated as advancing down superior vena cava 42 to access tumor 48, but depending on the location of the tumor, and possibly other factors, the catheter could alternatively be advanced up the portal vein 44 or the hepatic artery 46. Alternatively, a percutaneous approach could be used to advance the catheter to the tumor. Typically, catheter 10 is initially advanced towards tumor 48 with the aid of fluoroscopy and/or CAT scan guidance. Once close enough to tumor 48, ultrasound images from tumor ablation device 50 typically provide additional information for guiding catheter 10 to the tumor. FIG. 5A shows a schematic illustration of tumor ablation device 50 for treating tumor 48 in accordance with an embodiment of the present invention. Tumor ablation device 50 comprises a plurality of ultrasound transducers 52, which are each coupled to control bus 38 by a respective connection wire 56. (Only one connection wire 56 is shown for clarity.) Typically, device 50 comprises 48 ultrasound transducers, but devices comprising more or fewer are within the scope of the present invention (e.g., between 32 and 64 transducers). In the embodiment illustrated in FIG. 5A, the ultrasound transducers are in a circular array, such that when tumor ablation device 50 presses against tumor 48, the output of the various ultrasound transducers can be coordinated in a phased array mode so that the energy is pointed towards successive portions of the tumor. For some applications, ultrasound detection functionality is incorporated in tumor ablation device 50. In an embodiment, other imaging or detection functionalities are incorporated in tumor ablation device 50 or in another element, so as to facilitate assessments of tissue to target with ultrasound energy and tissue to avoid targeting with ultrasound energy.

Typically, tumor ablation device 50 comprises an ultrasound detector 54, which is used to obtain ultrasound images of tumor 48 prior to treatment. These images are then used to determine where the ultrasound energy should be directed so that ultrasound transducers 52 can be used as a phased array to maximize the treatment potential, while minimizing collateral damage. For example, a raster scanning algorithm or other algorithm may be used to ablate successive portions of the tumor, while minimizing the energy applied to surrounding tissues. Subsequent to each treatment, a new ultrasound image is typically but not necessarily obtained to assess the level of ablation and to determine whether more treatment is necessary, and if so to determine which portion of the tumor should be targeted.

Figure 5B:
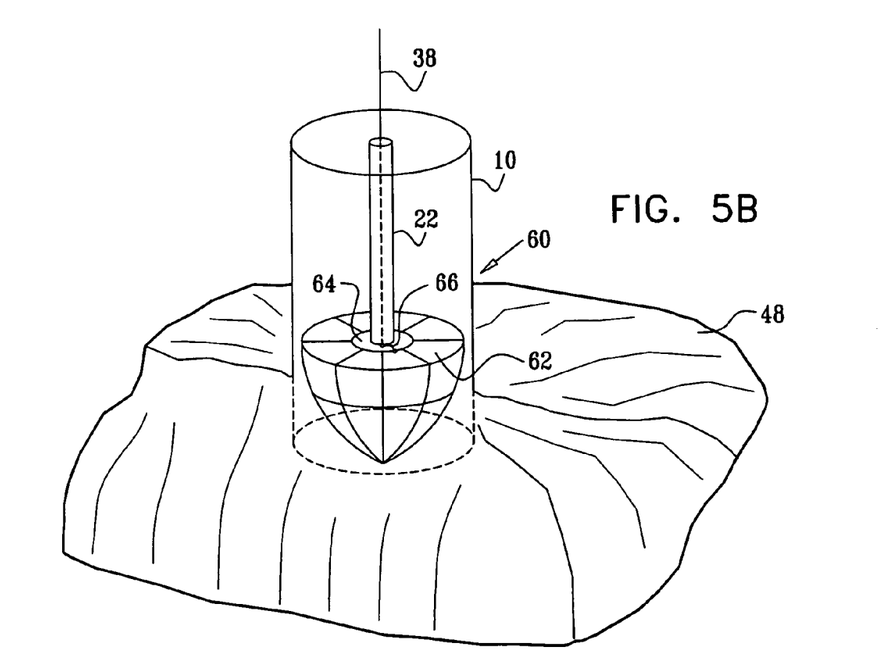

FIG. 5B shows a schematic illustration of a tumor ablation device 60 for treating tumor 48 in accordance with an embodiment of the present invention. Tumor ablation device 60 comprises a plurality of ultrasound transducers 62, which are each coupled to control bus 38 by a respective connection wire 66 and an ultrasound detector 64, allowing device 60 to function in the same manner as device 50 discussed hereinabove with reference to FIG. 5A. Device 60 is shaped like a hemisphere or a cone, so by applying mechanical pressure to the device, it can be pushed partially or completely into the tumor prior to or during treatment. This may be advantageous for both imaging the tumor and ablating the tumor with ultrasound. For some applications, ultrasound detection functionality is incorporated in tumor ablation device 60. In an embodiment, other imaging or detection functionalities are incorporated in tumor ablation device 60 or in another element, so as to facilitate assessments of tissue to target with ultrasound energy and tissue to avoid targeting with ultrasound energy.

It is noted that the techniques described hereinabove may be applied to isolate a pulmonary vein by ablating tissue within the left atrium and/or by ablating tissue within the pulmonary vein.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use with a subject, comprising:
   a catheter having a longitudinal axis and having a distal portion;
   an ultrasound array arranged to the distal portion of the catheter, the ultrasound array comprising a plurality of ultrasound transducers, the plurality of ultrasound transducers being circumferentially arranged around the longitudinal axis, and adapted to operate in a phased array mode to apply ablating energy to tissue of the subject located in a range of azimuths, with respect to the longitudinal axis, that is less than 360 degrees, the plurality of ultrasound transducers being configured to provide, in concert, a curved profile along the longitudinal axis of the catheter and adjacent to the distal portion of the catheter;
   a detection functionality adapted to determine a portion of the tissue of the subject that is not to be targeted by the ablating energy and a next successive portion of the tissue of the subject to be ablated; and a controlling functionality adapted to control the ultrasound array to set the range of azimuths responsive to the determination of the portion of the tissue that is not to be targeted and the next successive portion of the tissue of the subject to be ablated as determined by the detection functionality.

2. The apparatus according to claim 1, wherein the detection functionality comprises an ultrasound transducer.

3. The apparatus according to claim 1, wherein the detection functionality comprises at least a portion of the ultrasound array.

4. The apparatus according to claim 1, wherein the detection functionality comprises imaging functionality.

5. The apparatus according to claim 1, wherein the detection functionality is adapted to be fixed to the distal portion of the catheter.

6. The apparatus according to claim 1, wherein the detection functionality is adapted to operate external to a body of the subject.

* * * * *